United States Patent
Muenker

(10) Patent No.: US 8,273,078 B2
(45) Date of Patent: Sep. 25, 2012

(54) DEVICE FOR CREATING OPENINGS IN PRESSURIZED VESSELS WITH DEFORMABLE WALLS

(75) Inventor: Frank Michael Muenker, Utrecht (NL)

(73) Assignee: AMJ bv (NL)

( * ) Notice: Subject to any disclaimer, the term of this patent is extended or adjusted under 35 U.S.C. 154(b) by 1219 days.

(21) Appl. No.: 12/042,386

(22) Filed: Mar. 5, 2008

(65) Prior Publication Data

US 2008/0249516 A1 Oct. 9, 2008

Related U.S. Application Data

(60) Provisional application No. 60/892,946, filed on Mar. 5, 2007.

(51) Int. Cl.
*A61B 18/20* (2006.01)
(52) U.S. Cl. .................. 606/10; 606/7; 606/153
(58) Field of Classification Search ............... 606/7, 10, 606/153
See application file for complete search history.

(56) References Cited

U.S. PATENT DOCUMENTS

| 5,725,544 | A | 3/1998 | Rygaard |
|---|---|---|---|
| 5,964,750 | A | 10/1999 | Tulleken et al. |
| 6,080,175 | A | 6/2000 | Hogendijk |
| 6,740,098 | B2 * | 5/2004 | Abrams et al. ............ 606/148 |
| 2002/0049459 | A1 | 4/2002 | Kato |
| 2002/0128602 | A1 | 9/2002 | Adams et al. |
| 2004/0255952 | A1 * | 12/2004 | Carlsen et al. .......... 128/207.14 |

FOREIGN PATENT DOCUMENTS

| DE | 4408746 A1 | 9/1995 |
|---|---|---|
| EP | 750476 | 9/1995 |
| EP | 0938871 A2 | 9/1999 |
| EP | 1 907 152 E1 | 12/2010 |

OTHER PUBLICATIONS

"European Application No. 08152300.3, Decision to Grant a European Patent Pursuant to Article 97(1) EPO mailed Nov. 11, 2010", 7 pgs.

* cited by examiner

*Primary Examiner* — Henry M Johnson, III
*Assistant Examiner* — Jeffrey Lipitz
(74) *Attorney, Agent, or Firm* — Schwegman Lundberg & Woessner, P.A

(57) ABSTRACT

The catheter (1) has a fastener (10) for firmly holding the wall (19) of vessel (18) when it is cut by optical fibers (3). The fastener (10) has an engaging element which can be a pin (20), roughened surface (23), spiral grooves (27), dendritic grooves (31), adhesive surface (34) or pointed pins (38).

17 Claims, 12 Drawing Sheets

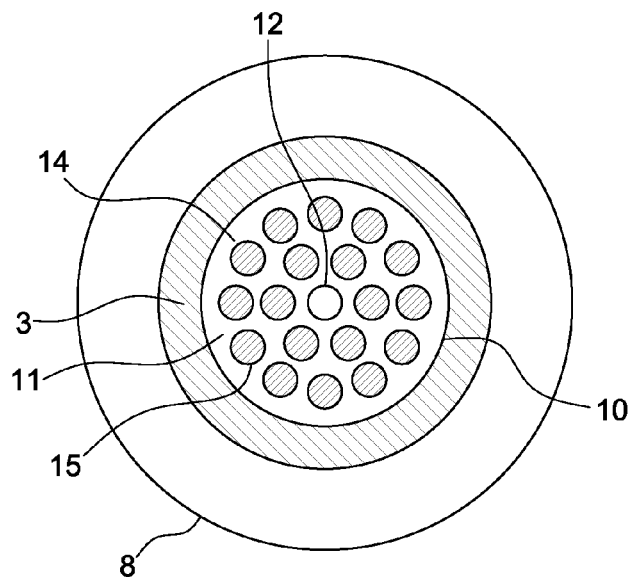
FIG. 1b
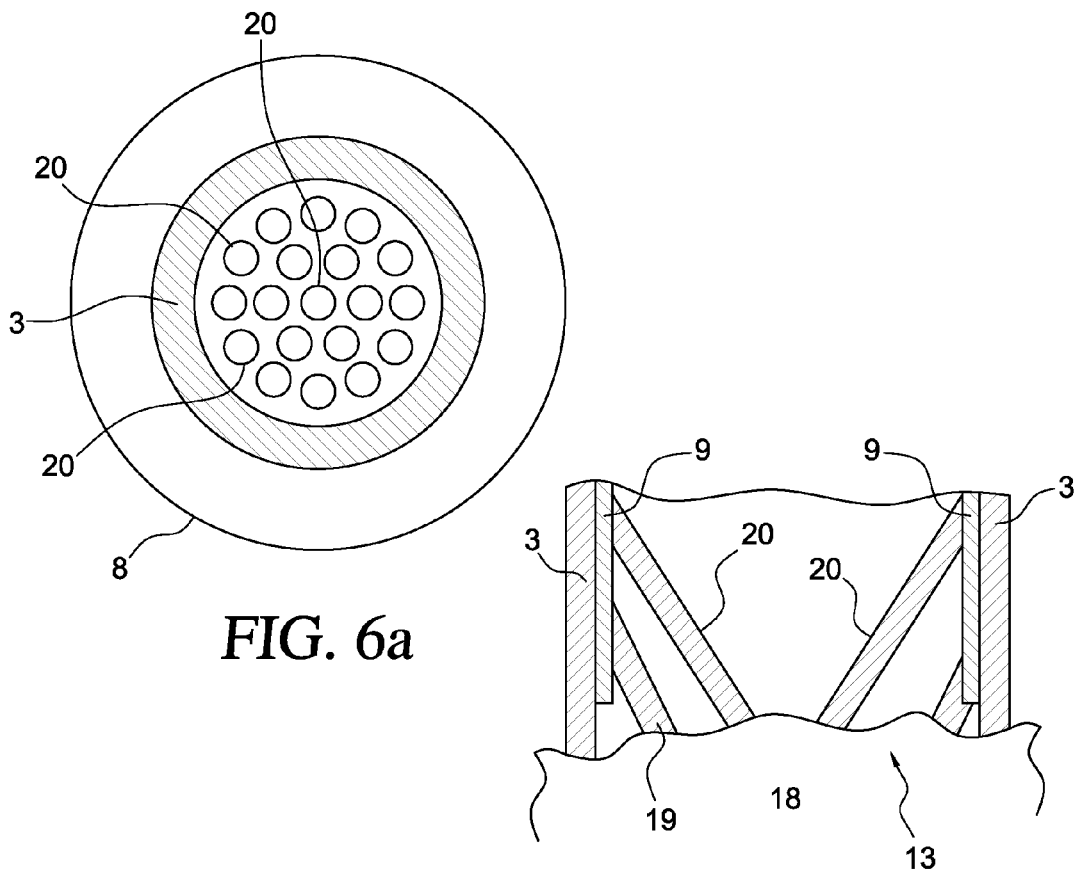
FIG. 6a
FIG. 6b

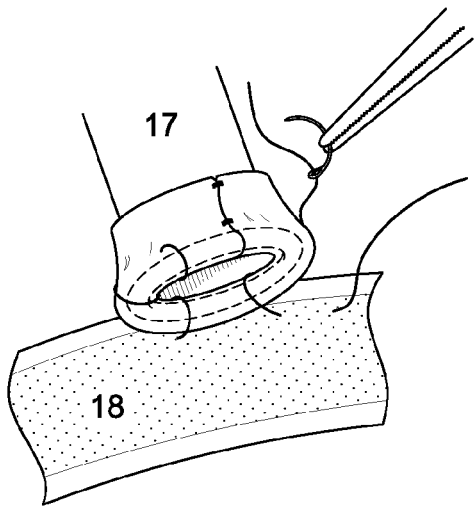 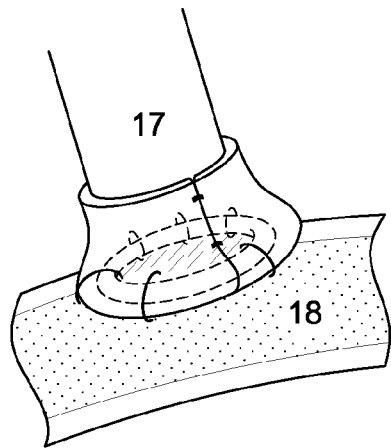
FIG. 3a    FIG. 3b
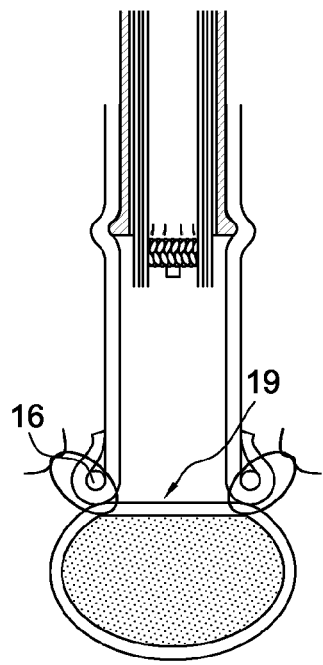
FIG. 3c

DEVICE FOR CREATING OPENINGS IN PRESSURIZED VESSELS WITH DEFORMABLE WALLS

CROSS REFERENCE

This application claims priority under 35 U.S.C. §119(e) to U.S. Provisional Patent Application No. 60/892,946, filed Mar. 5, 2007, entitled "DEVICE FOR CREATING OPENINGS IN PRESSURIZED VESSELS WITH DEFORMABLE WALLS", the disclosure of which is incorporated by reference herein in its entirety.

FIELD OF THE INVENTION

The present invention relates to a device and a method to create openings in the wall of intracorporal vessels while the vessels are under pressure, and more particularly for the creation of arteriotomies.

BACKGROUND OF THE INVENTION

There are increasing possible uses of devices, such as laser catheters, in surgery due to the growing number of different structural designs of laser catheters and their distal end regions. For instance, laser catheter tips are known which can, in particular, be employed in bypass surgery and which are especially distinguished by the fact that the cross section of the distal end of the laser catheter at which the light exists is completely composed of optical fibers. Such catheters are referred to, by way of illustration, as "full multifiber catheters".

With the aid of the aforementioned type of catheter, techniques for laser-aided anastomosis (surgical joining of two hollow organs, such as, attaching an additional blood-carrying channel (bypass) to a bloodchannel artery whose flow cross section is narrowed by deposits) are known, which permit bypass surgery without interrupting the blood flow in the main artery. For instance, the ELANA (Excimer Laser Assisted Nonocclusive Anastomosis) operating technique, developed by neurosurgeon C. A. F. Tulleken and described in U.S. Pat. No. 5,964,750 and EP 0 750 476, deals with a surgical technique for creating an arteriotomy in which a catheter creates a geometrically exactly predefined hole in the wall of a vessel and at the same time ensures that separated remains of the vessel do not stay in the blood stream. U.S. Pat. No. 5,964,750 is incorporated herein by reference in its entirety.

First a bypass vessel is connected to the outer circumference of the vessel to be treated. Through this bypass vessel, a laser catheter tip, which is designed elastically at the distal end, is inserted and positioned within the bypass vessel, onto the outer wall of a pressurized intracorporal vessel to be treated. The catheter is provided with a perforated member disposed at its distal end, capable of transmitting vacuum suction which is created in the lumen. The catheter creates an opening in the pressurized intracorporal vessel by cutting along a closed line (generally a circle) and holding on to the vessel wall cut out by vacuum (or low pressure) suction. Through this opening, part of the blood flow can be diverted through the bypass vessel around the obstruction in the treated vessel.

In addition to the great advantage of being able to conduct bypass surgery without interrupting the pressurized intracorporal vessel, which is especially vital in bypass surgery in the brain, this surgical technique has several drawbacks. For example, as the vessel wall is under pressure and is put under additional tension by surgical suturing and by the vacuum suction within the catheter, the tension is such that as the vessel wall is being cut, the vessel wall can cause the cut-out piece of vessel wall to be pulled sideways. The resulting movement of the vessel wall can cause the cut to be ineffective, and thus the cut tissue remains attached. Additionally, the movement can also cause fluid (such as blood, or gases in other circumstances) to be drawn into the lumen, thereby increasing the pressure within the lumen and thus reducing the force with which the vessel wall is being held to the perforated member. Thus, in some of these cases, the cut is not complete and a piece of vessel wall (a "flap") remains attached to the rest of the vessel wall and retained rather than adhering to the perforated member and being retrieved out of the body with the catheter.

Thus, it is desirable that a device for creating arteriotomies be designed to reduce the incidence of retained flaps.

OBJECTS OF THE INVENTION

It is therefore an object of the present invention to design a device that firmly holds the surface of that portion of the wall of the vessel to be treated to prevent movement of the vessel wall across the distal end of the catheter.

Another object of the present invention is to not perforate the vessel wall when firmly holding the wall of the vessel.

These and other objects and advantages are achieved by the present invention as described herein.

SUMMARY OF THE INVENTION

The present invention achieves these objects by using a fastener in the bore or lumen of the catheter at the distal end of the catheter. The fastener makes it possible to provide high resistance to movement of the vessel wall across the distal end of the catheter without perforating the vessel wall.

The creation of arteriotomies according to the invention generally requires a catheter and a bypass vessel with a ring affixed to one end. The arteriotomy site must generally be prepared with microsurgery techniques using the ring end of the bypass vessel before the arteriotomy is made with the catheter.

The catheter according to the invention has a cutting device which is disposed in a ring-shaped configuration, and is provided at the outer circumference of its distal end with a circumference-widening element past which the cutting device extends. With this arrangement of the cutting device, the distal tip of the cutting device thus assumes the form of a planar, ring-shaped area.

The element widening the outer circumference of the catheter serves basically as a type of stopper or stop device which permits the surgeon to determine when the distal end of the ring-shaped cutting device has reached the maximal penetration depth in the bypass vessel and made contact with the wall of the vessel which is to be cut. The surgeon must terminate the penetration procedure at the latest when the edge of the outer circumference of the widening elements comes into contact with the outer wall of the vessel adjacent the ring. By the stop device coming into contact with the outer wall of the vessel covering the ring, the vessel to be treated is pressed into the same shape as the design of the stop device, ensuring that the cutting device rest evenly on the wall of the vessel to be treated.

The stopper also aids in centering the catheter in the bypass vessel and centering the cutting device with respect to the spacer.

Alternatively, the distal end of the cutting device abuts the wall of the vessel to be treated and this signals to stop the forward motion of the catheter. In such a case, the stopper is not needed.

The fastener disposed at its distal end of the catheter's lumen or bore firmly holds the portion of the vessel wall to be cut, once vacuum suction is applied through the bore of the catheter. The fastener does not protrude farther than the planar, ring-shaped area of the cutting device, thus causing the wall of the vessel to flex inward into the bore, the fastener along with the vacuum firmly hold the wall of the vessel.

Furthermore, the ring-shaped arrangement of the cutting device permits separation of a circular disk of the wall vessel which is deposited inside the catheter. If the catheter is carefully extracted from the cut vessel wall, no remains stay in the blood circulation system, because the circular, separated piece of vessel wall is held inside the catheter, by means of the low pressure prevailing therein.

Broadly, the device of the present invention can be defined as a catheter for performing arteriotomies on intracorporal vessels comprising
(a) a tubular body having a proximal end, and a distal end;
(b) a ring shaped cutting device positioned at the distal end of the tubular body for cutting a hole in a wall of a vessel in need of treatment;
(c) a bore inside the tubular body and the cutting device; and
(d) a fastener positioned in the bore at the distal end of the bore, the fastener adapted to firmly hold a portion of the wall of the vessel that forms the hole when a vacuum is applied through the bore and the hole is cut in the wall of the vessel by the cutting device.

Suitably, the cutting device is a laser device, a high frequency device, an ultrasound cutting device or a mechanical cutting device. Preferably, the cutting device is a laser device and, more preferably, the laser device is optical fibers extending outward from the distal end of the tubular body.

Preferably, the tubular body has an inner sleeve, an outer sleeve and an annulus between the inner sleeve and the outer sleeve; and
the cutting device is optical fibers which are positioned in the annulus and form a ring that extends outward from the distal end of the tubular body.

Suitably, the fastener is a porous member mounted in the bore with an engaging element on a surface of the porous member which faces the distal end of the bore. The engaging element is suitably one or more protrusions extending outward from the porous member toward the distal end of the cutting device but not extending past the planar, ring shaped area defined by the distal end of the cutting device. The engaging element is also suitably a surface treatment for firmly holding the cut portion of the treated vessel. Such surface treatments include various grooved surfaces, an adhesive surface, and/or a roughed surface. The treated surface faces the planar ring shaped area defined by the distal end of the cutting device. Combinations of these engaging elements can be used.

Suitably, the engaging element can also be pointed protrusions, however, the pointed protrusions can not perforate the wall of the vessel to be treated till after the portion of the wall of the vessel to be treated has been cut away. Suitably, the points will engage the cut away portion of the wall as it is cut away.

The porous member is suitably a perforated plate, a porous fabric, wire mesh, grids, sieves, porous ceramic, porous stone, foam, 2D packing of hollow tubes or massive cylinders, 3D packaging spheres, or a supporting structure that supports the engaging element and allows for passage of vacuum suction.

Further a suitable fastener includes pins affixed at one end to the inner wall of the tubular body and extending towards the planar ring shaped area defined by the distal end of the cutting device but do not extend beyond the planar area.

The ring-shaped cutting device defines an inner surface which is an endless loop that is suitably circular or oval. The bore also defines an inner surface which is an endless loop, which is also suitably circular or oval, however, it can also be square or rectangular, provided it is able to allow the vacuum to travel from the proximal end to the distal end of the catheter. The preferred shape of the inner surface for both the bore and the cutting device is circular.

In order for the fasteners to firmly hold the wall of the vessel, a vacuum suction is applied through the bore.

Broadly, the method of the present invention can be defined as a method for performing bypass surgery on intracorporal vessels comprising:
providing a catheter having a tubular body having a proximal end, and a distal end, a ring shaped cutting device positioned at the distal end of the tubular body, a bore inside the tubular body and the cutting device, and a fastener positioned in the bore at the distal end of the bore;
attaching a rigid spacer to an end of a bypass vessel;
attaching the end of the bypass vessel to an outer surface of a wall of a vessel which is to be treated;
inserting the catheter into the bypass vessel until the cutting device abuts the wall;
applying vacuum suction through the bore to firmly hold a portion of the outer surface of the wall of the vessel against the fastener;
cutting a hole in the held portion of the wall;
and removing the catheter with the cut portion of the wall held by the fastener.

Preferably, the catheter has a stopper on the outside wall of the tubular body at the distal end and the catheter is inserted into the bypass vessel until the stopper abuts the spacer.

Suitably, the spacer is a ring and the method further comprises
placing the ring over the bypass vessel;
folding an end portion of the bypass vessel back on itself over the ring; and
attaching the end portion to retain the ring, forming a rigid end of the bypass vessel.

The step of attaching the spacer to the end of the bypass vessel and the step of attaching the end of the bypass vessel to the treated vessel can suitably be accomplished in any conventional manner such as sewing, suturing, gluing with an adhesive or a combination thereof. It will also be recognized that the method for attaching the spacer to the bypass vessel and the method to attach the bypass vessel to the treated vessel can be different.

Where the fastener is a porous member with pointed protrusions, the points of the protrusion can contact but not perforate the wall until after the wall is cut away from the vessel.

The protrusions are preferably at least half as long as the vessel wall is thick. The protrusion extends essentially perpendicularly to the vessel wall. With such dimensioning, the protrusions exerts friction on the elastic vessel wall, without perforating the vessel wall, and prevents the vessel wall from sliding across the surface.

Furthermore, the distance from the porous member to the planar, ring-shaped end area of the cutting device corresponds at least to the thickness of the treated vessel wall. With such dimensioning, the elastic vessel wall is sucked to the bottom side of the porous member by the low pressure (vacuum suction) prevailing inside the bore, in an advantageous manner. Consequently, on the one hand, the end area of the cutting device comes fully into contact with the surrounding vessel wall and, on the other hand, the vessel wall lies largely very close to the inner profile yielded by the ring-shaped cutting device and the porous member in order to ensure circular separation of the vessel wall.

Furthermore, according to the present invention, the separation procedure can be optimized by the catheter tip's engaging, during application of the cutting, with a particularly disposed ring-shaped element, on the one hand ensuring that the separation of the piece of the vessel wall occurs completely and on the other hand preventing any further injury to vessel walls, (such as to the opposite vessel wall of the blood-carrying artery). The ring-shaped element is joined to the bypass channel independent of the catheter tip in such a manner that the vessel wall is made taut during application of the cutting. Thus, the ring-shaped cutting catheter tip rests evenly on the vessel wall, which is a prerequisite for a homogenous cutting.

The device and method according to the invention thus permits from exterior of a vessel wall, high resistance to movement of the vessel wall across the surface of the obstruction without perforating the vessel wall. Consequently, retained flaps caused by ineffective cutting of the vessel wall are completely eliminated.

In an especially advantageous embodiment, if the bore, which is surrounded by the ring-shaped cutting device and is joined to a low pressure source, is provided at its distal end with a perforated member having an arrangement of concentrically disposed boreholes therein and a cylindrical pin perpendicularly protruding from the center. Such even suction achieved by the boreholes with such a pin hinders the deformable surface to be cut (e.g., the vessel wall) in such a manner that a complete defined hole is created in the vessel.

Other objects, advantages and novel features of the present invention will become apparent from the following detailed description of the invention when considered in conjunction with the accompanying drawings.

BRIEF DESCRIPTION OF THE DRAWINGS

FIGS. 1a and 1b show respective views of an embodiment of the catheter tip according to the invention.

FIGS. 3a, 3b and 3c show a schematic representation of various steps in attaching the bypass to a vessel wall to be treated;

FIGS. 6-16 illustrate alternative fasteners of the present invention.

DETAILED DESCRIPTION OF THE DRAWINGS

Figure 1A:
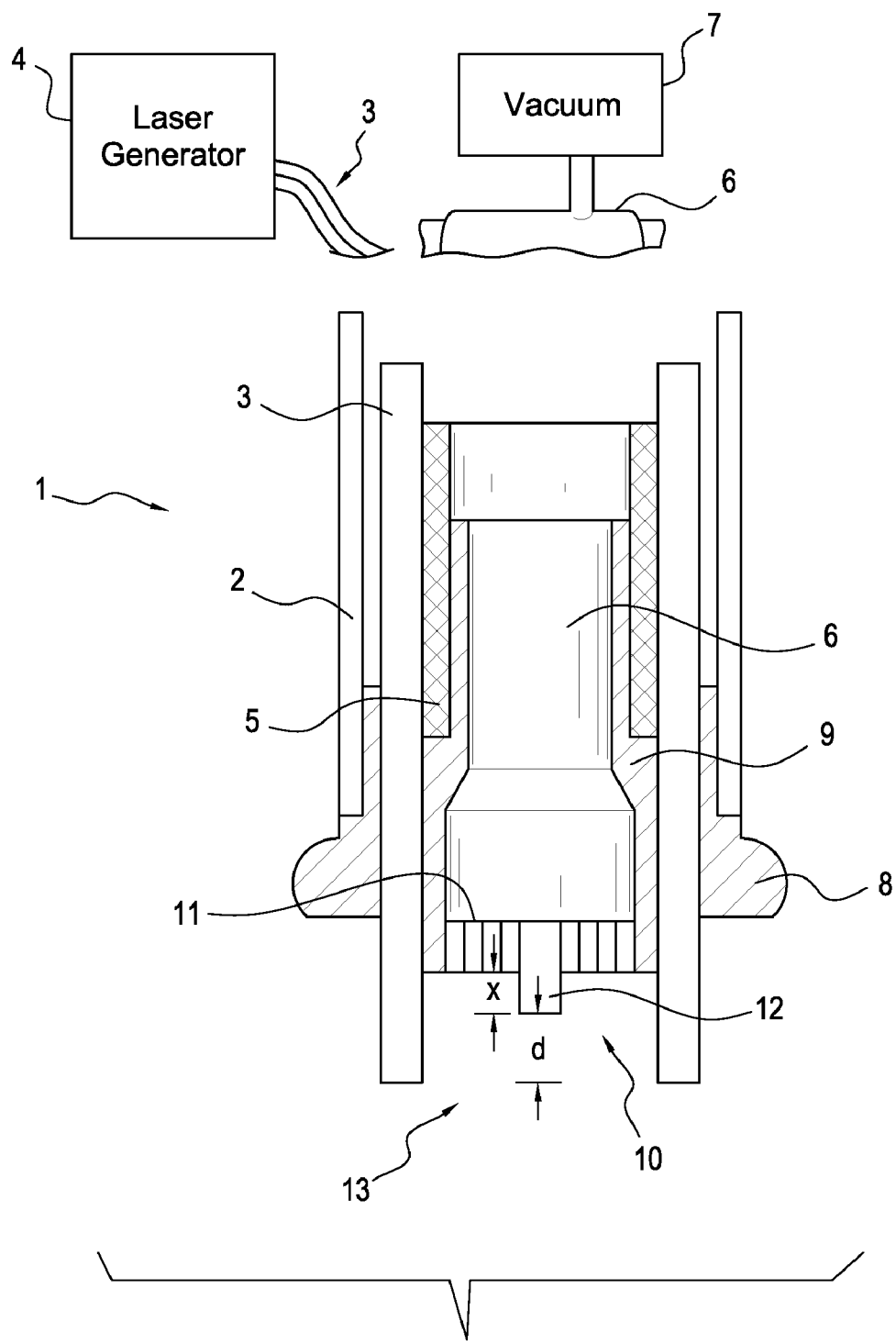

FIGS. 1a and b show cross sectional representations and a bottom view of the distal region of laser catheter 1 according to the invention. Laser catheter 1 has outer casing 2, which meets the typical demands for use in the medical field, such as easy sterilization, high flexibility and material compatibility. Outer casing 2 surrounds the ring-shaped arrangement of optical fibers 3 which are disposed in two layers, in two concentric circles in the preferred embodiment and are connected to laser generator 4. Inner tube-shaped casing 5 surrounds bore 6, which is joined at its proximal end to a low pressure source 7. At the tip of the distal region of laser catheter 1, is outer circumference-widening element 8, which in the preferred embodiment has an atraumatic ring-shaped cross section, with a straight stop edge in the direction of the distal end. The dimensioning of the outer-circumference widening element 8 must be such that the outer circumference of element widening the outer circumference of laser catheter 1 has at least the diameter of the vessel channel through which the laser catheter is to be guided. In this way, it is ensured that the catheter tip is centered inside the vessel channel in a self-guiding manner by resting with its circumference on the inside area of the vessel channel.

In the direction of the distal end of the laser catheter tip, the ring-shaped optical fibers 3 project beyond the plane of the widening element 8. The optical fibers 3 for their part surround a holding means 9, which represents on the distal end a termination for the inner casing 5 but which, in particular provides, a holding device for a fastener 10 which comprises porous member 11 which leads to the low pressure prevailing inside bore 6 and protrusion 12, which extends towards the distal end of bore 6, not beyond the plane of the light exit area 13. Bore 6 extends to the distal end of fibers 3. A bottom view of the laser catheter tip in FIG. 1b shows an advantageous arrangement of porous member 11 with plate 14 and perforation holes 15, which are disposed in concentric circles, and of protrusion 12, which is a cylindrical pin disposed in the center of the porous member 11. FIG. 1b shows the circumference area of the element 8 widening the outer circumference of the fibers 3.

The laser catheter of the present invention preferably has optical fibers arranged to form a plane circle with an outer diameter of about 2 mm. At a distance of no further than the plane of light exit area 13, the porous member 11 is set inside optical fibers 3. Protrusion 12 extends no further than the plane of the optical fibers 3, i.e. no further than the plane of light exit area 13. Thus, the protrusion is 0% or 0 mm from the light exiting area. In certain embodiments distance d in FIG. 1b corresponds to about 10% to 120% of the diameter of the bore, including about 20%, 30%, 40%, 50%, 60%, 70%, 80%, 90%, 100% and about 110%. In a certain embodiment, the protrusion 12 is about 0.05 to 0.6 mm from light exit area 13 as shown by measured distance d in FIG. 1a. In a further embodiment, the protrusion 12 is about 0.2 to 0.4 mm from light exit area 13. In the form depicted in FIG. 1a, the protrusion 12 is a cylindrical pin. Preferably, the pins are blunt pins, preferably blunt pins having a flat tip rather than a rounded tip.

Preferably, the length of the blunt pins which extends from the plate is about 0.1 to 5 times, preferably about 0.5 to 2 times as long as the vessel wall is thick. For large intercerebral vessels the pin or other protrusion should be have a length x of about 0.05 to about 0.6 mm and, more preferably, about 0.1 to 0.3 mm or about 0.2 to 0.4 mm.

For a closer description of the manner of working of the laser catheter tip according to the invention, FIGS. 2 to 5 illustrate schematically the manner of applying it to carry out bypass surgery without interrupting the blood flow within the blood-carrying vessel.

Figure 2A:
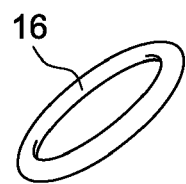
FIGS. 2a, 2b, 2c and 2d show preliminary measures for carrying out bypass surgery using the catheter tip according to the invention.
Figure 2A:
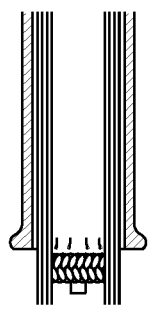

FIG. 2a shows the laser catheter tip designed according to the present invention above which a ring-shaped element 16 is shown, the diameter of which is larger than the outer diameter of the ring-shaped disposed optical fibers and smaller than (or the same size as) the diameter of the element 8 widening the outer circumference of the laser catheter. Usually the inner diameter of the ring (made, for example, of a body-compatible platinum-iridium alloy or pure platinum) is about 2.6 to 2.8 mm.

In preparation for bypass surgery, the ring is slipped over a bypass vessel 17, which is taken from a different region of the body of the patient so that the surgical joining of such removed vessel, (such as a piece of artery) as a bypass for the blood-carrying vessel, is not complicated or prevented by the body's own rejection. Alternatively, bypass vessel 17 can be an artificial vessel instead of a donor vessel taken from the patient, animal or other person.

Figure 2B:
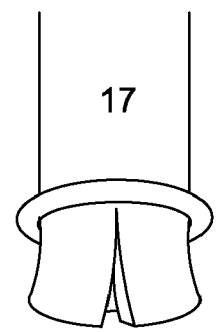
Figure 2C:
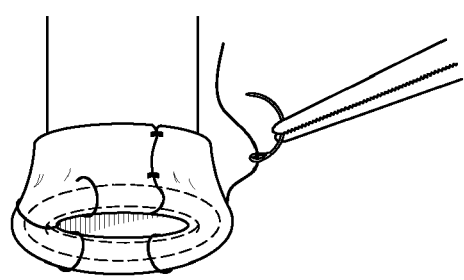
Figure 2D:
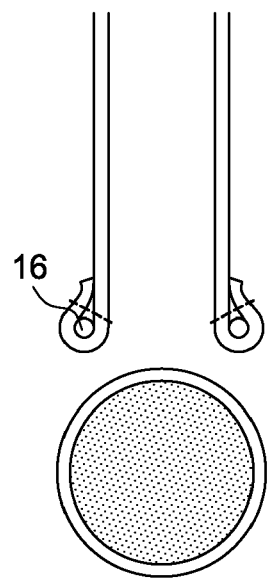

According to FIG. 2b, subsequently the removed artery is everted about the ring or an incision is made into the removed artery, which is then wrapped upward about the ring 16 and sewn around the latter, in the manner shown in FIGS. 2c and 2d. In this way, a stable end of the vessel is obtained which according to FIG. 2d assumes the outer contour of ring 16 in a stable form.

Next, the vessel 17, thus prepared, is joined to the outer surface of the vessel channel 18 to be treated, by means of a ring-shaped seam, as shown in FIG. 3a. In the state according to FIG. 3b, the bypass vessel 17 rests firmly on the surface of the vessel 18 which is to be treated. Then the invented laser catheter is guided through the inside of the vessel channel 17 in the direction of the vessel wall 19 of the vessel 18, a portion of which is to be severed. As FIG. 3c shows, the vessel wall 19 is made taut for attaching the bypass, due to the ring 16 in such a manner that the distal end of the laser catheter can be placed on a plane area. This has the advantage that during laser light application, the vessel wall 19 is impinged evenly with laser light in the contact region with light exit area 13. In this way, even material ablation at the vessel wall 19 is ensured.

Figure 4A:
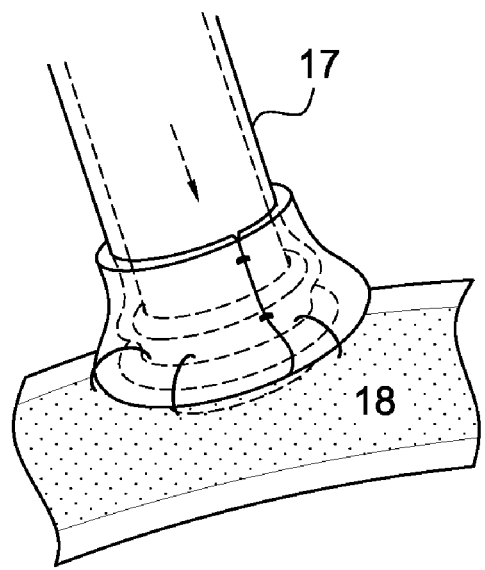
FIGS. 4a, 4b and 4c illustrate the manner of function of the catheter tip according to the invention during light application.
Figures 4B, 4C:
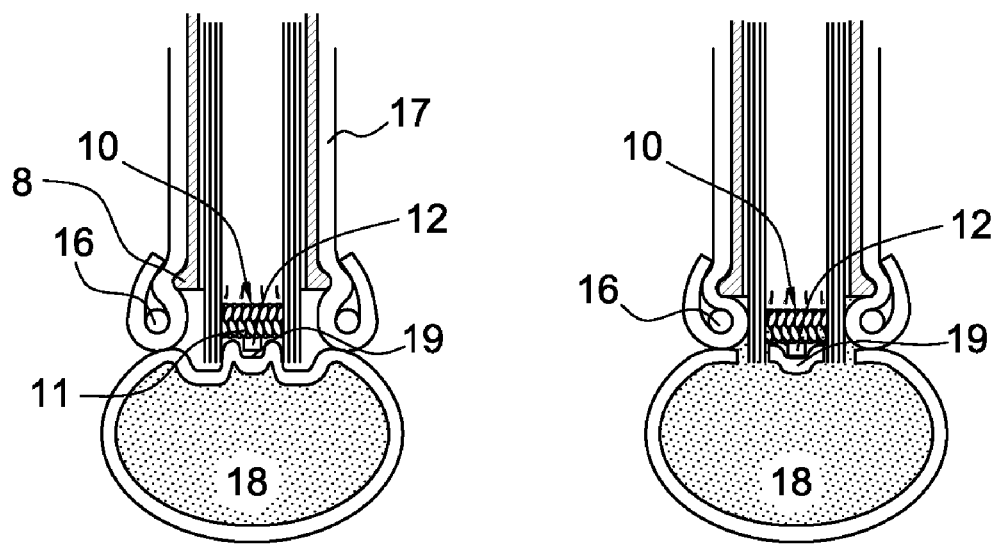

FIG. 4a shows a perspective representation of the connection of the vessels 17 and 18 as well as the entry of the laser catheter tip through the vessel 17. The laser catheter tip is, as depicted in FIG. 4b, first guided through vessel 17 until light exit area 13 of the distal laser catheter rests on the vessel wall 19 to be separated. Thereafter, low pressure source 7 connected to the bore 6 is activated and ensures that the separated piece of vessel wall 19 is drawn to the surfaces of the fastener 10.

Now laser light source 4 is activated (in the present application, preferably an excimer laser for generating ultra-violet radiation). The laser is operated in pulses with a repetition frequency of e.g. 40 Hz, for about 5 seconds, so that about 200 pulses with an energy of about 10 mJ impinge upon the tissue. The laser catheter tip thus slowly penetrates the lumen of the vessel 18 until the stop edge of the element 8 widening the outer circumference of the laser catheter touches the wall of vessel 17 which is pressed inside by ring 16. Thus as shown in FIG. 4c, the piece of the vessel wall 19 is separated from the remaining wall of the vessel 18, and adheres to the surface of the fastener 10.

Figure 5A:
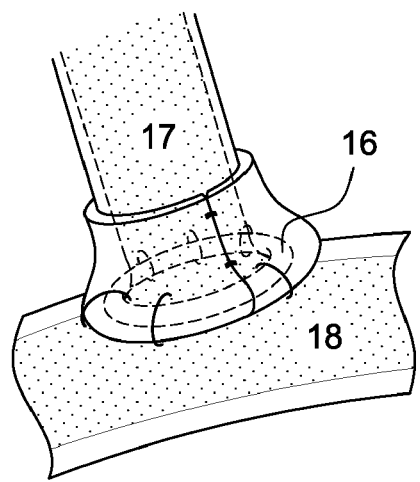
FIGS. 5a and 5b show the removal of the separated vessel wall by means of the catheter.
Figure 5B:
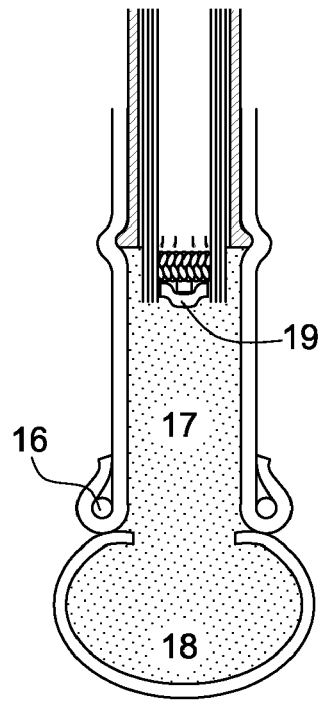

According to FIGS. 5a and 5b, the blood can now flow through the vessel channel 17 after the distal end of the laser catheter has been removed from the bypass vessel channel 17, together with the separated piece of vessel wall 19. Ring 16 remains continuously at the bypass connection between the vessel channels 17 and 18.

By means of the invention, it is possible to conduct bypass surgery with creating a complete defined hole in blood vessels to be treated without perforating the vessel unintentionally and without interrupting the flow through and without removing the pressure in the treated vessel. With the aid of the invented laser catheter tip, precise penetration of the vessel walls can be made without leaving remains of the vessel walls in the blood stream, which might obstruct narrow sites in the blood stream. Without further limitation of any possible applications of the described catheter tips in the filed of medicine, the device can be utilized with any intracorporal vessels, in particular, for bypass surgery in the coronary vessels of the heart.

Because of undulating or curved pattern produced by the vacuum suction, porous member 11 and protrusion 12, as illustrated in FIGS. 4 and 5, wall 19 is held firmly in place and does not move when wall 19 is cut.

It will be understood that more than one pin can be used in fastener 10.

FIGS. 6-11 illustrate views of addition embodiments of the fastener of the present invention.

FIGS. 6a and 6b illustrate a fastener which is a multiplicity of pins 20 fixed on the inner wall of holding means 9 and extending downward toward area 13. Pins 20 do not extend past area 13 and allow the vacuum in bore 6 to pull wall 19 into bore 6 in a manner similar to fastener 10. Because of the plurality of pins 20, wall 19 is held by pins 20 in place in an undulating manner similar to fastener 10 as shown in FIG. 6b.

FIGS. 7-15 illustrate fastener which have a porous member and different distal end surface treatments for firmly holding wall 19 in place during cutting.

Figure 16:
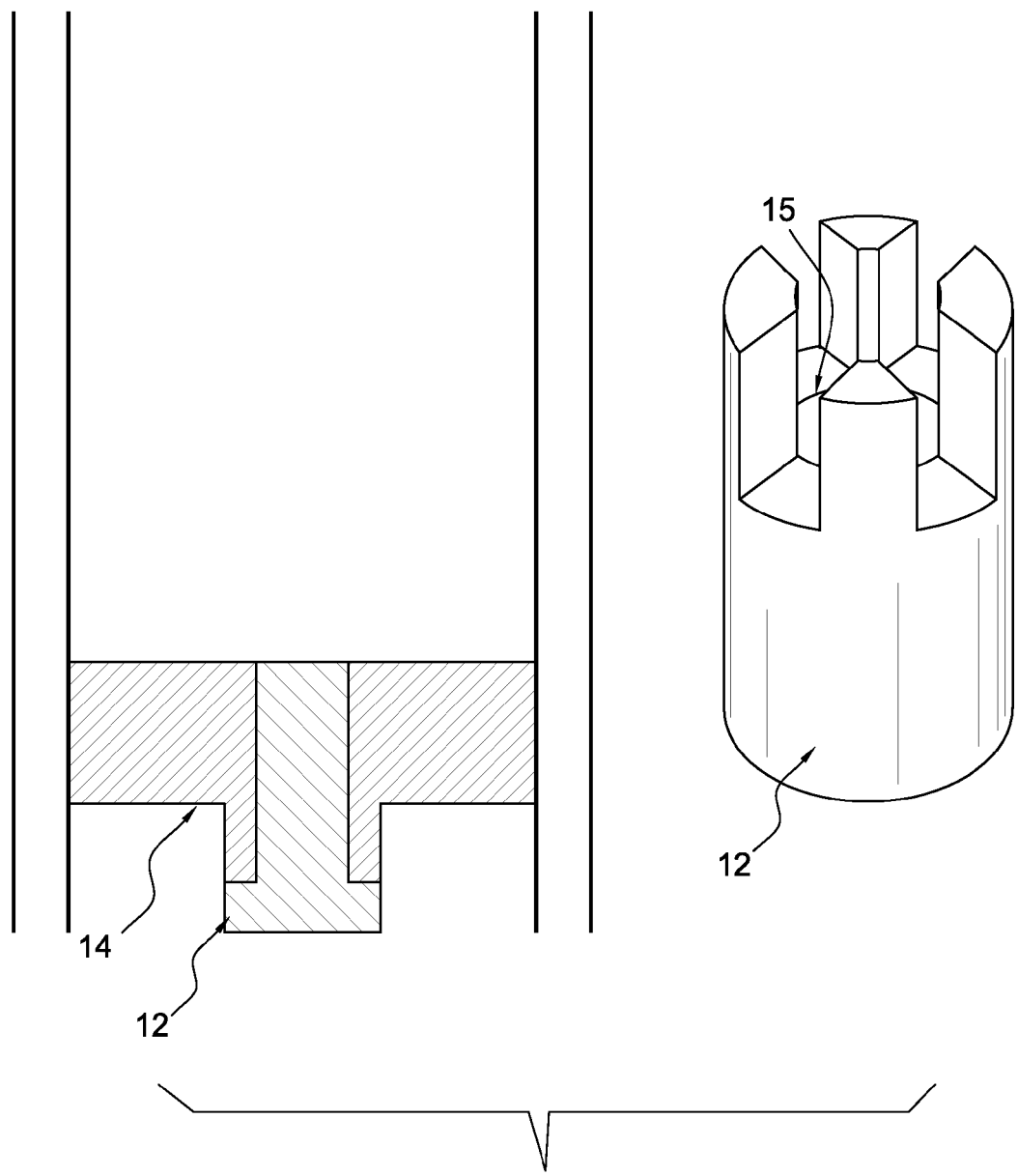

FIG. 16 illustrates a fastener which has a porous member which has been, at least in part, merged with a protrusion.

Figure 7:
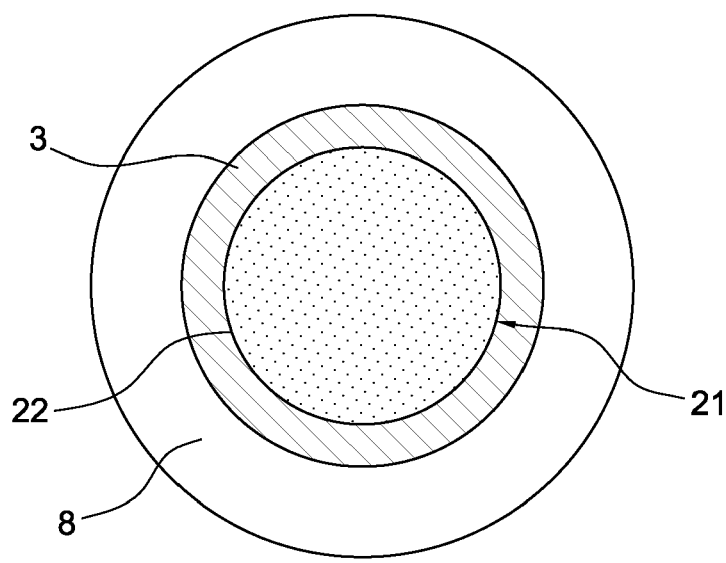

FIG. 7 illustrates a bottom view of fastener 21 with porous fabric 22 which may have a surface treatment which faces area 13. When vacuum is applied to bore 6, wall 19 is pulled against the surface of the fastener and held firmly in place during cutting. Porous fabric 22 allows gas but not liquid to flow, i.e. the porous fabric is gas permeable and liquid impermeable.

Figure 8A:
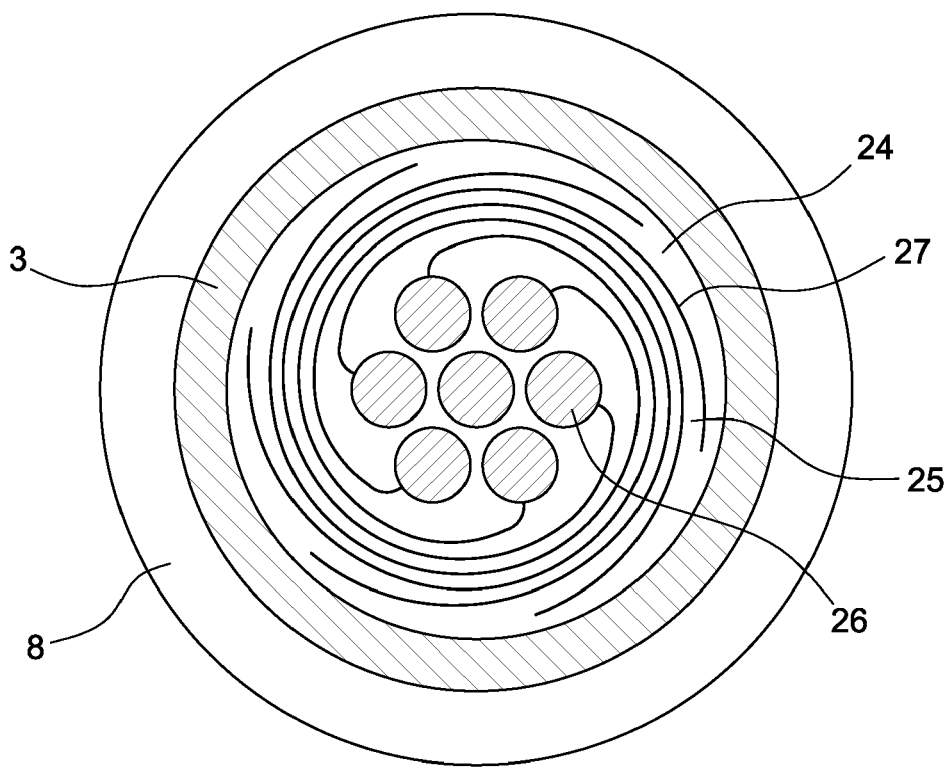
Figure 8B:
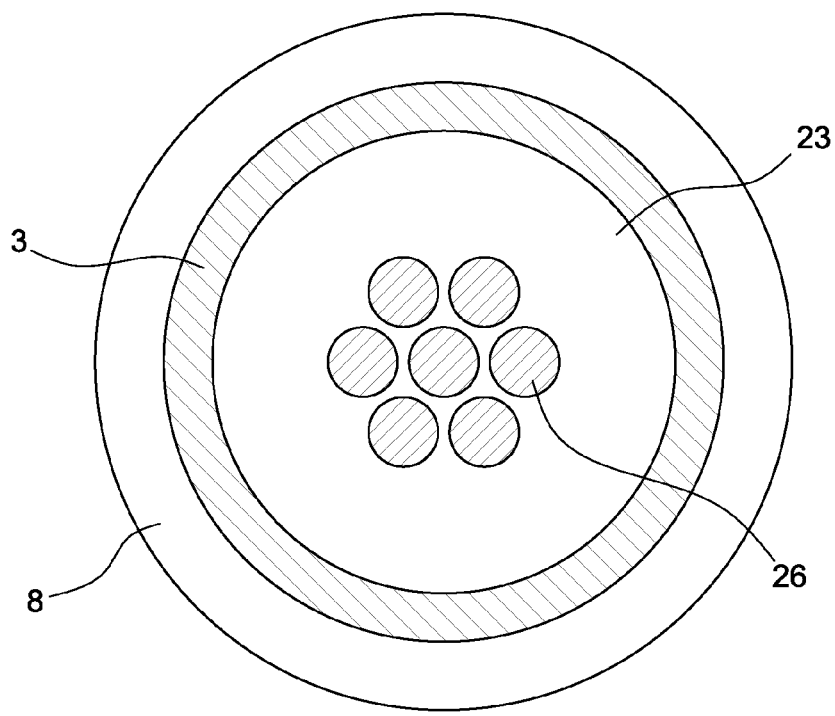

FIG. 8a illustrates fastener 24 with a porous member being plate 25 with holes 26 and spiral grooves 27 emanating therefrom. Spiral grooves 27 are cut into the distal end of plate 25 and face area 13. Vacuum suction pulls wall 19 into contact with grooves 27 and the frictional force between wall 19 and grooves 27 hold wall 19 firmly during cutting thus, friction prevents wall 19 from sliding sideways during cutting. FIG. 8b corresponds to the embodiment shown in FIG. 8a. However, a roughened surface 23 rather than grooves surround the holes 26. Vacuum suction pulls wall 19 into contact with roughened surface 23 and the frictional force between wall 19 and roughened surface 23 hold wall 19 firmly during cutting thus, friction prevents wall 19 from sliding sideways during cutting.

Figure 9:
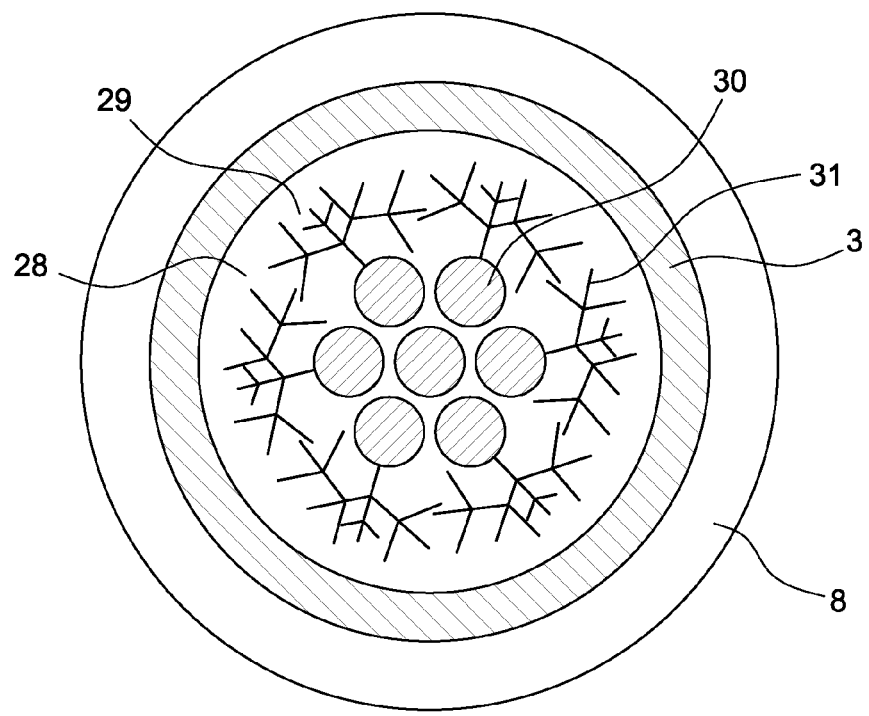

FIG. 9 illustrates fastener 28 with a porous member being plate 29 with holes 30 and dendritic grooves 31 emanating therefrom. Vacuum pulls wall 19 into contact with groove 31 and the frictional force between wall 19 and groove 31 hold wall 19 firmly during cutting.

FIGS. 8 and 9 are also examples (compare FIGS. 12 to 15) in which holes, here 26 and 30, are located in a central portion of the plate rather than being evenly spread over its surface. Preferably, a rim around this central portion of the plate is non-porous. The rim may have a surface that is grooved in one or more ways, adhesive, roughened or a combination thereof. This rim can extend over about 10%, 20%, 30%, 40%, 50% or about 60% of the radius of the plate. As can be seen from, e.g., FIGS. 12 to 15, this embodiment can also comprise a pin, which is preferably located at the centre of the plate. The non-porous rim part provides the advantage that, in case the cut portion of the wall of the vessel is not covering the rim part completely, no liquid or gas will be sucked into the bore by the low pressure prevailing in the bore, which would result in reduction of the holding force acting on said cut portion.

Figure 10:
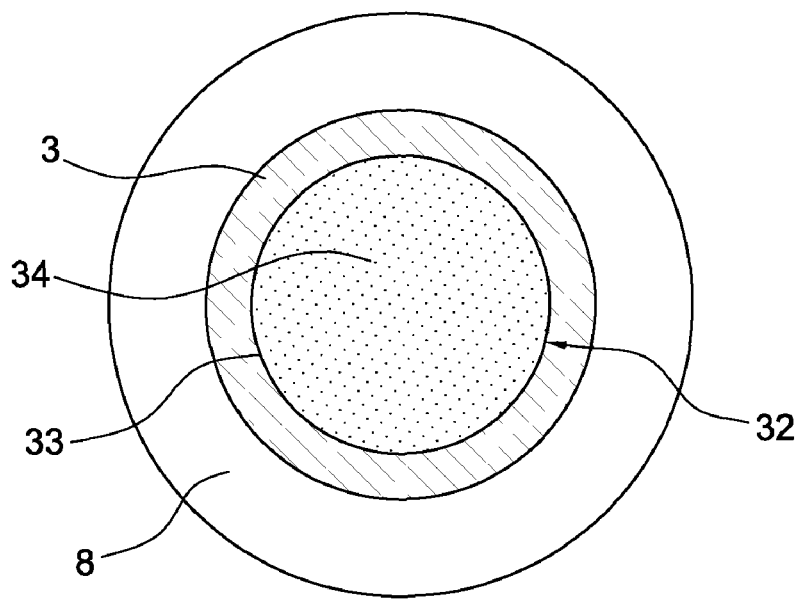

FIG. 10 illustrates fastener 32 with porous fabric 33 having adhesive surface 34. When vacuum pulls wall 19 against adhesive surface 34, wall 19 is held firmly during cutting.

Figure 11:
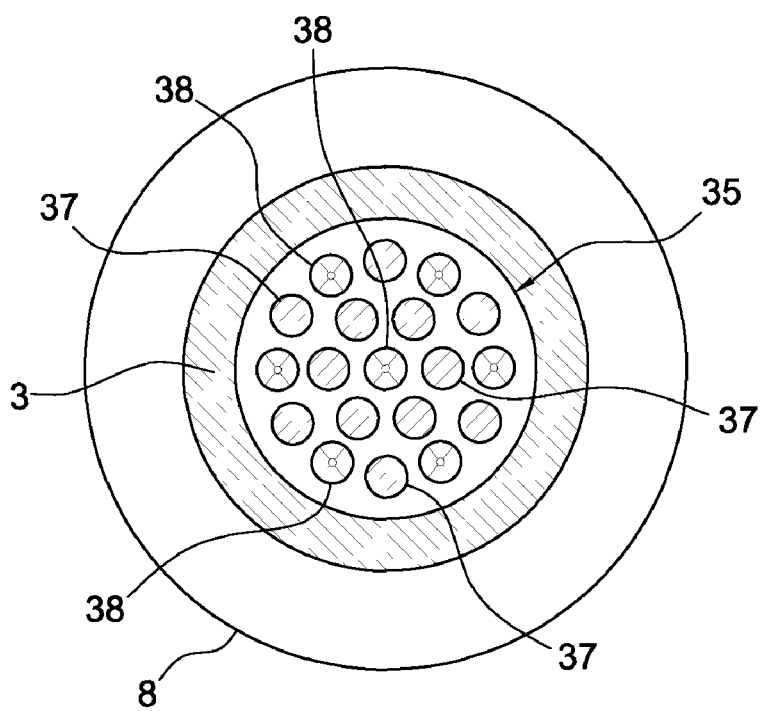

FIG. 11 illustrates fastener 35 being plate 36 with holes 37 and pointed pins 38. Pointed pins 38 firmly engage wall 19 when vacuum is applied through bore 6 and holes 37 so efficient holding is obtained.

Figure 12:
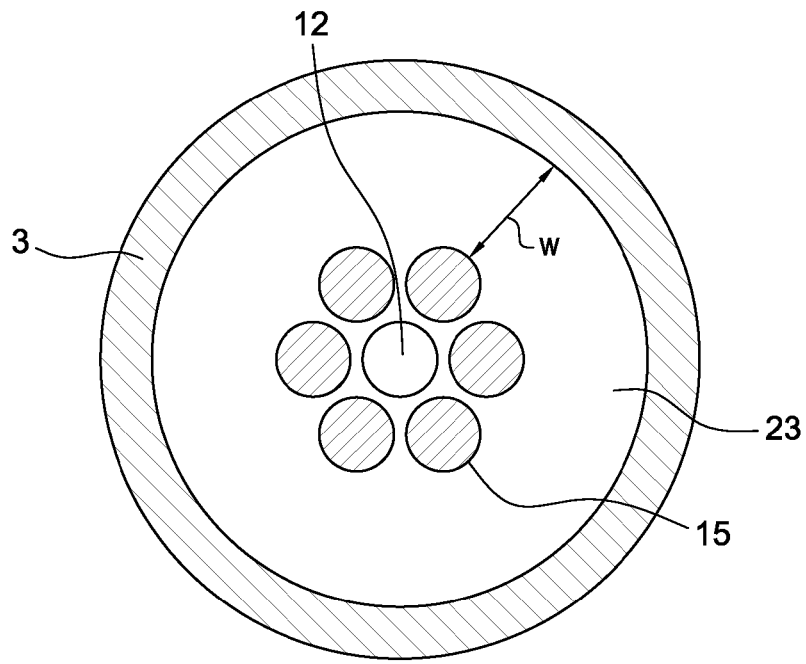

FIG. 12 illustrates a combination of protrusion 12 and roughened surface 23 for the engaging surface of the fastener. Width (w) defines the width of the rim already discussed above (FIGS. 8 and 9). In this embodiment, in use, the inherent tension of the wall of the vessel to be treated and the further tension caused by the protrusion, will cause the tissue to shrink towards the protrusion upon cutting, exposing the outer part of the plate (rim). The non-porous rim thus provides a barrier against liquids entering the catheter. The width (w) of the rim may be about 70%, 80%, 90% or preferably about 100% or more of length x of the protrusion. The length x of the protrusion preferably does not exceed a length defined by the distal radius of the bore r(b) and the radius of the porous member r(pm) minus w. E.g. if the inner distal diameter of the bore is 1.6 mm, the length x of the protrusion should generally not exceed 0.4 mm. However, shorter protrusions such as protrusions having half that length, in the above example a length x of 0.2 mm, are also within the scope of the present invention.

Figure 13:
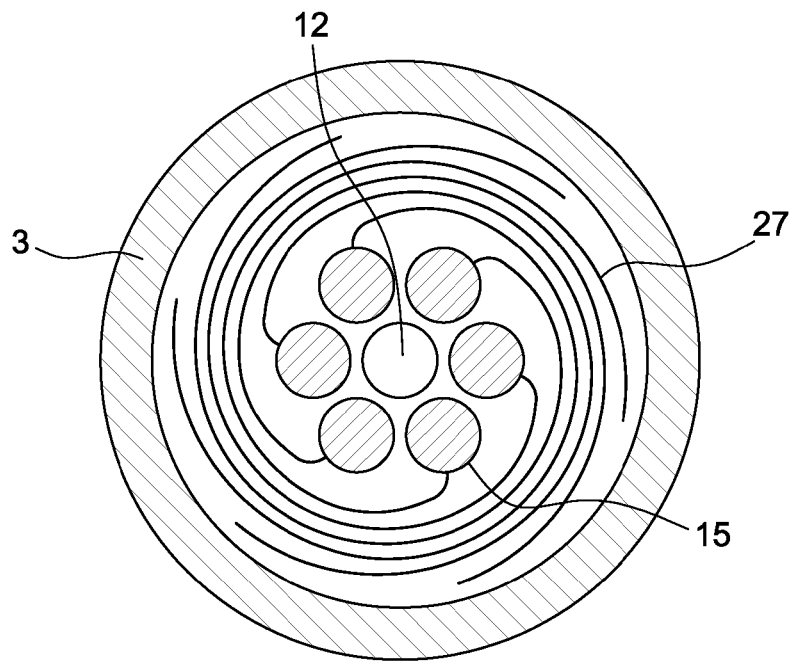

FIG. 13 illustrates a combination of protrusion 12 and spiral grooves 27 for the engaging surface of the fastener.

Figure 14:
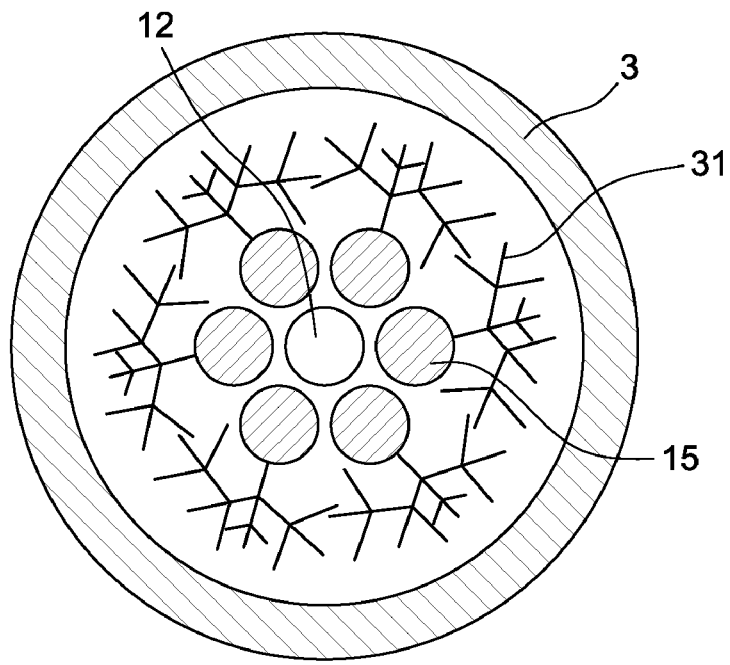

FIG. 14 illustrates a combination of protrusion 12 and dendritic grooves 31 for the engaging surface of the fastener.

Figure 15:
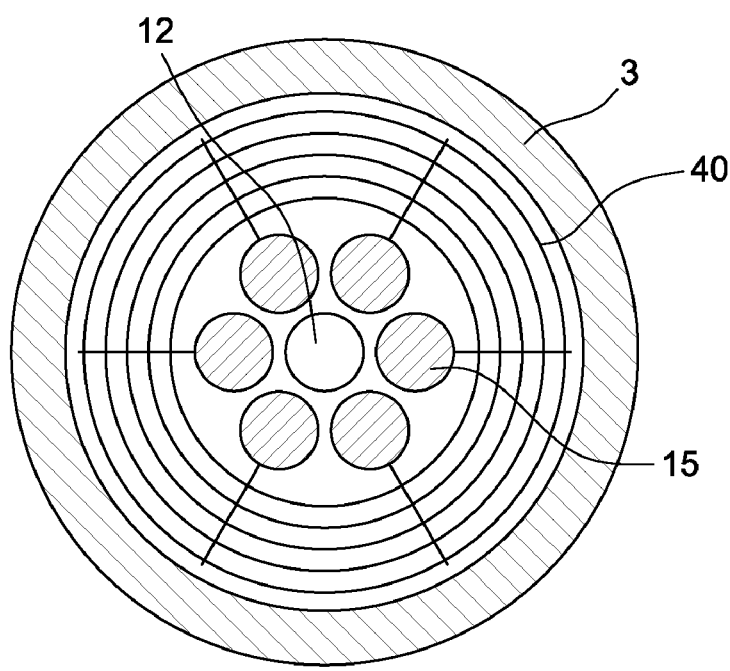

FIG. 15 illustrates a combination of protrusion 12 and symmetrical grooves 40 for the engaging surface of the fastener.

FIG. 16 shows an embodiment in which the protrusion 12, shown as a blunt pin with a flat tip, is merged with the porous member. In the embodiment shown, there is a single hole 15 (channel) at the centre of the pin so that the pin becomes a hollow tube 12 extending from plate 14 as shown. This hollow tube may take a multitude of configurations. In certain embodiments, the distal part of the tube may have a larger circumference/inner diameter than the part proximal to the plate, e.g., about 10%, 20% 25% or 30% larger. The distal part of the hollow tube may also be perforated or otherwise establish a passage between the interior of the tube and its surrounding when in use. Alternatively, and as shown in FIG. 16, the distal part of the hollow tube may comprise vertical cuts. However, the direction of these cuts can vary. Thus, these cuts may be at an angle, e.g., an angle of about 10°, 20° or 30° relative to the axis of the hollow tube 12. Any cuts, perforations or similar at the distal part of the hollow tube should not cover, when measured from the tip of the protrusion, more than an area (A) defined by the distal radius of the bore of the catheter r(b) minus the radius of hole 15 r(h) of the protrusion (A=r(b)−r(h)). In certain embodiments the area (A) is about ⅔ (r(b)−r(h)). When the device is in use tissue covering area (A) will prevent blood from entering the catheter. The hollow tube preferably comprises one or more surface treatments as described above and/or outward pointing spikes. In the embodiment shown in FIG. 16, plate 14 may be non-porous or, at least in part, porous. The diameter of hole 15 may be about 25% of the distal diameter of the bore of the catheter.

The roughened surface can have an average roughness (Ra) of about 10 to about 100 micrometers. Suitably, the whole or a part of the distal surface of the porous member is roughened.

Any conventional means can be used for roughening the surface such as sand blasting or rubbing with abrasive material.

The roughened surface can be essentially flat near the center but in a cross section inclines towards the edge of the bore. The diameter of the holes in the perforated plate is preferably 0.05 to 0.3 mm. Also, one or more engaging element can be used, e.g., a pin and a roughened surface or pins and grooves.

In a preferred embodiment, the fastener is a perforated plate with a center pin. The plate is positioned in the bore at a depth of at least about equal to the diameter of the bore hole and, more preferably, about twice the bore hole. The center pin extends a length from the plate equal to about 40 to about 100% of the distance from the plate to the exit area. The center pin preferably has a diameter of about 0.2 mm or about 10% of the diameter of the bore. The holes in the plate are evenly spaced around the pin and preferably have a diameter of about 0.05 to about 0.3 mm. The plate may comprise a rim. The number of holes in the plate is preferably 1 to 20 and, more preferably, 4-10. Preferably, the surface of the plate, around the pin, such as the rim, is roughened with deep, narrow grooves. Preferably, the grooves intersect each other and may intersect the holes. Preferably, the grooves have a depth of about 0.005 to about 0.1 mm and a width of about 0.001 to about 0.05 mm. The grooves preferably have sharp edges to help hold the wall of the vessel.

Although the invention has been described and illustrated in detail, it is to be clearly understood that the same is by way of illustration and example, and is not to be taken by way of limitation. The spirit and scope of the present invention are to be limited only by the terms of the appended claims.

REFERENCE CHARACTERS

| | |
|---|---|
| 1 | laser catheter |
| 2 | outer casing |
| 3 | optical fibers |
| 4 | laser generator |
| 5 | inner casing |
| 6 | bore |
| 7 | vacuum |
| 8 | widening element |
| 9 | holding means |
| 10 | fastener |
| 11 | porous member |
| 12 | protrusion |
| 13 | exit area |
| 14 | plate |
| 15 | holes |
| 16 | ring |
| 17 | by pass vessel |
| 18 | vessel to be treated |
| 19 | wall of vessel |
| 20 | pins |
| 21 | fastener |
| 22 | porous member |
| 23 | roughened surface |
| 24 | fastener |
| 25 | plate |
| 26 | holes |
| 27 | spiral groove |
| 28 | fastener |
| 29 | plate |
| 30 | holes |
| 31 | dendritic grooves |
| 32 | fastener |
| 33 | porous fabric |
| 34 | adhesive surface |

| | | |
|---|---|---|
| | -continued | |
| | d—distance | |
| 35 | fastener | |
| 36 | plate | |
| 37 | holes | |
| 38 | pointed pin | |
| 40 | symmetrical grooves | |

I claim:

1. A catheter for performing arteriotomies on intracorporal vessels comprising:
 (a) a tubular body having a proximal end and a distal end;
 (b) a ring shaped cutting device positioned at the distal end of the tubular body for cutting a hole in a wall of a vessel to be treated;
 (c) a bore inside the tubular body and the cutting device; and
 (d) a fastener positioned in the bore at the distal end of the bore, the fastener adapted to firmly hold a portion of the wall of the vessel that forms the hole when a vacuum suction is applied through the bore and the hole is cut in the wall of the vessel by the cutting device;
  wherein the fastener is a porous member mounted in the bore and a protrusion extends outward from the member towards the distal end of the bore.

2. The catheter of claim 1 wherein
 the cutting device is a laser device.

3. The catheter of claim 2 wherein
 the laser device is optical fibers which form a ring that extends outward from the distal end of the tubular body.

4. The catheter of claim 1 wherein
 the tubular body has a stopper on an outside wall of the tubular the distal end of the tubular body.

5. The catheter of claim 1 wherein
 the tubular body has an inner sleeve, an outer sleeve and an annulus between the inner sleeve and the outer sleeve; and
 the cutting device is optical fibers which are positioned in the annulus and form a ring that extends outward at the distal end of the tubular body.

6. The catheter of claim 1 wherein
 the fastener comprises a porous member mounted in the bore and a protrusion extending outwardly from the member towards the distal end of the bore wherein the protrusion is a plurality of protrusions.

7. The catheter of claim 1 wherein
 the fastener is a porous member having grooved surface facing the distal end of the bore.

8. The catheter of claim 1 wherein
 the fastener is a porous member having an adhesive surface facing the distal end of the bore.

9. The catheter of claim 1 wherein
 the fastener is a porous member having a roughened surface facing the distal end of the bore.

10. The catheter of claim 1
 wherein the fastener comprises a protrusion that is at least one pin and extends from the plate a distance of about 0.1 to 5 times of a wall thickness of the intracorporal vessel and the distal end of the pin is about 0% to 120% of the inner diameter of the bore from the planar area defined by the distal end of the cutting device.

11. The catheter of claim 10, wherein the pin extends from the plate a distance of about 0.5 to 2 times of the wall thickness of the intracorporal vessel.

12. The catheter of claim 10, wherein the distal end of the pin is about 0% to 40%, preferably about 5% to 30% or about 10% to 25% of the inner diameter of the bore from the planar area defined by the distal end of the cutting device.

13. The catheter of claim 1, wherein the fastener comprises a porous member having a porous central portion and a non-porous rim surrounding the porous central portion, and wherein, viewed in radial direction of the bore, the rim extends over at least 10% of the radius of the bore.

14. The catheter of claim 6, wherein the protrusion is a pin and wherein the fastener comprises a porous member having a porous central portion and a non-porous rim surrounding the porous central portion, and wherein a width of the rim is about 70% or more of the length of the pin.

15. The catheter of claim 13, wherein the rim has a surface that is grooved and/or roughened and/or adhesive.

16. The catheter of claim 14, wherein the rim has a surface that is grooved and/or roughened and/or adhesive.

17. The catheter according to claim 1, wherein the fastener comprises a plate positioned in the bore and a protrusion fixed to the plate and extending towards the distal end of the bore, wherein the protrusion is provided with a channel extending from the proximal side of the plate to the distal end of the protrusion and wherein the distal end of the protrusion is optionally provided with cuts extending from the channel in a radial direction of the bore.

* * * * *

UNITED STATES PATENT AND TRADEMARK OFFICE
CERTIFICATE OF CORRECTION

| | | |
|---|---|---|
| PATENT NO. | : 8,273,078 B2 | Page 1 of 1 |
| APPLICATION NO. | : 12/042386 | |
| DATED | : September 25, 2012 | |
| INVENTOR(S) | : Frank Michael Muenker | |

It is certified that error appears in the above-identified patent and that said Letters Patent is hereby corrected as shown below:

On the Title Page, Item (56)

Column 2, under "Foreign Patent Documents", line 4, delete "1 907 152 E1" and insert --1967152 B1--, therefor Column 2, under "Other Publications", line 2, delete "EPO" and insert --EPC--, therefor In the Claims In column 11, line 24-26, in Claim 1, after "device", delete "; wherein the fastener is a porous member mounted in the bore and a protrusion extends outward from the member towards the distal end of the bore", therefor In column 11, line 35, in Claim 4, after "tubular", insert --body at--, therefor Signed and Sealed this
Twenty-fifth Day of November, 2014

Michelle K. Lee
*Deputy Director of the United States Patent and Trademark Office*